United States Patent [19]
Frassica et al.

[11] Patent Number: 5,483,951
[45] Date of Patent: Jan. 16, 1996

[54] WORKING CHANNELS FOR A DISPOSABLE SHEATH FOR AN ENDOSCOPE

[75] Inventors: Jim Frassica, Chelmsford; Robert Ailinger, Norwood, both of Mass.

[73] Assignee: Vision-Sciences, Inc., Natick, Mass.

[21] Appl. No.: 201,571

[22] Filed: Feb. 25, 1994

[51] Int. Cl.⁶ .................................................. A61B 1/00
[52] U.S. Cl. .................... 600/104; 604/282; 600/121; 600/139; 600/156
[58] Field of Search .................. 128/4, 11, 6; 604/282, 604/265

[56] References Cited

U.S. PATENT DOCUMENTS

| | | | |
|---|---|---|---|
| 4,676,229 | 6/1987 | Krasnicki et al. | 128/4 |
| 4,947,827 | 8/1990 | Opie et al. | 128/4 |
| 5,025,778 | 6/1991 | Silverstein et al. | 128/4 |

FOREIGN PATENT DOCUMENTS

WO93/058-42  4/1993  WIPO .

*Primary Examiner*—Richard J. Apley
*Assistant Examiner*—Beverly M. Flanagan
*Attorney, Agent, or Firm*—Seed and Berry

[57] ABSTRACT

An endoscopic sheath assembly having an endoscope tube and a plurality of working channels, wherein the endoscope tube is adapted to receive and tightly surround a flexible, elongated endoscope that has a neutral bending plane. Working channels, including a biopsy channel, an air channel, and a water channel, are disposed within and substantially parallel to the endoscope tube along its length radially outward of the neutral bending plane of the endoscope. The biopsy, air, and water channels each have proximal sections and expansion sections. The suction channel has a proximal section comprising a lubricious inner tube forming a lubricious inner lumen, and a kink resistant outer tube bonded to the inner tube. The expansion section of the biopsy channel has a close pitch, axially wound, flat wire spring tightly surrounded by an extruded elastomeric material that is adapted to maintain radial compression force on the spring member. The flat wire spring forms a durable, lubricious inner lumen of the expansion section of the suction/biopsy channel. The air and water channels have a proximal section formed by a flexible, kink-resistant polyvinyl chloride tube, and an expansion section constructed of a thick-walled elastomeric extrusion that is adapted to axially expand and contract as the channels bend during endoscope articulation. A spirally wound wrap secures the biopsy, air, and water channels together along their distal sections.

31 Claims, 4 Drawing Sheets

WORKING CHANNELS FOR A DISPOSABLE SHEATH FOR AN ENDOSCOPE

TECHNICAL FIELD

This invention relates to the field of endoscopy, and more particularly, to endoscope isolation assemblies having working channels therein.

BACKGROUND OF THE INVENTION

The use of endoscopes for diagnostic and therapeutic indications is rapidly expanding. To improve performance, endoscopes have been optimized to best accomplish their purpose. Therefore, there are upper endoscopes for examination of the esophagus, stomach, and duodenum; colonoscopes for examining the colon; angioscopes for examining blood vessels, bronchoscopes for examining the bronchi; laparoscopes for examining the peritoneal cavity; and arthroscopes for examining joint spaces. The discussion which follows will apply to all of these types of endoscopes.

Instruments to examine the rectum and sigmoid colon, known as flexible sigmoidoscopes, are good examples of the usefulness of endoscopic technology. These devices are expensive, and they are used in a contaminated environment for a brief procedure (5–10 minutes) to screen symptomatic and asymptomatic patients for colon and rectal cancer. Typically, these endoscopes have a flexible insertion tube that is inserted into a patient during an endoscopic procedure. During insertion, the position of the distal end of the insertion tube is controlled by control devices on the endoscope's handle at the proximal end of the insertion tube. The distal end of the insertion tube must be sufficiently flexible to bend through tight radius corners during insertion.

The endoscopes also have multiple channels that extend along the length of the endoscope and come into contact with body tissues and fluids during the endoscopic procedure. These channels allow air insufflation into a body cavity, water flow to wash the endoscope's tip, suction through the tip, and biopsies to be taken. The channels must be sufficiently flexible to bend with the insertion tube through the short radius turns. The channels also must substantially maintain their cross-sectional shape and resist kinking around the tight turns to assure continuous the air flow, water flow, suction, and biopsy capabilities throughout the procedure.

Endoscopic accessories that, for example, take tissue samples are inserted through one of the channels, known as a biopsy channel, and extend beyond the insertion tube's distal end. The endoscopic accessories typically have elongated flexible shafts and a tool operatively connected to the shaft's distal end. The shaft must be longer than the endoscope to extend through the biopsy channel; for example, in colonoscopy, the sigmoidoscope is up to 2 meters long. Accordingly, the biopsy channel must allow for the passage of the endoscopic accessory therethrough without binding or hanging up around the short radius corners. The biopsy channel also must be constructed to avoid damage by the accessory's tool during its passage, and to provide minimum frictional resistance between the biopsy channel's inner lumen and the endoscopic accessory.

Endoscope assemblies have incorporated channels, such as the biopsy channel, within the insertion tube so the longitudinal axis of the channel is coaxially aligned with neutral bending plane of the insertion tube. Additionally, the conventional endoscope channels can slide axially within the insertion tube of the endoscope during articulation. As a result, the amount of expansion and contraction the axial sidewalls of the channel experiences is minimized during acute endoscope articulation. Thus, the forces causing the channel to kink are minimized. Conventional working channels have thick walls along their entire length and are sufficiently stiff to obtain a degree of kink resistance. Additionally, the thick wall provides a more wear resistant surface as endoscopes typically have a four year life during which several thousand procedures can be performed. Conventional channels are typically manufactured from Teflon® which provides a high degree of lubricity but needs added support in the bending section to articulate without kinking.

Endoscopes have used biopsy channels with Teflon forming the inner lumen along the entire length of the channel to provide increased lubricity. However, the Teflon channels are not sufficiently durable for multiple endoscopic procedure and cleaning cycles. In addition, the Teflon channels have limited flexibility and axial expansion characteristics, and they are expensive to manufacture.

As disclosed in U.S. Pat. No. 4,676,229, other endoscopes have an integral biopsy channel with an internal lubricious layer of material forming an inner lumen that is disposed within and supported by an axially wound filament. A blanket material fills the area between the windings of the filament, and a kink resistant yet stiff outer coating surrounds the filament and blanket material. This sandwiched filament construction is also coaxially aligned with the neutral bending plane of the endoscope, and it extends along the entire length of the biopsy channel, resulting in a relatively stiff structure that allows a minimum degree of axial expansion or contraction of the channel's sidewalls during acute endoscope articulation. In addition, this construction results in a complex and heavy assembly that is expensive to manufacture.

Those endoscopes having integral working channels along the neutral bending plane are severely contaminated during an endoscopic procedure. Proper cleaning and sterilization of the insertion tube and the integral work channels is very laborious and costly, thereby reducing the cost effectiveness of performing the therapeutic or diagnostic endoscopic procedures.

Disposable endoscopic sheaths have been developed to alleviate the problem of cleaning and sterilizing the working channels. The disposable sheaths fit over the insertion robe and completely isolate the insertion tube from the contaminating environment. The isolated insertion tube does not have integral working channels, but does contain a visual imaging device, illumination devices, and the control wires that bend the insertion tube's distal end. Working channels, such as air, water, and biopsy/suction channels, are disposed within the sheath adjacent to the isolated insertion tube and are open of the sheath's distal end to allow passage of air, water, suction or endoscopic accessories through the channels.

As a result, these working channels are positioned radially outward of the neutral bending plane of the insertion tube. When the insertion tube is bent around a short radius corner, the working channels must bend about the radially spaced neutral bending plane of the insertion tube so the axial sidewalls of the working channels are subject to significant axial expansion and compression forces which may cause kinking. Accordingly, the working channels must be axially flexible so the axial walls will expand and contract and will not kink or substantially resist the bending action of the insertion tube.

The Teflon biopsy/suction channel with the sandwiched filament section as well as the air and water channels discussed above are not suitable for use in such an endoscope/sheath assembly, because they are not sufficiently flexible and axially expandable. As a result, they would either kink or they would exert too much resistance to bending of the insertion tube around tight corners. Additionally, their construction is too expensive for a disposable product.

Accordingly, there is a need to provide an endoscopic sheath assembly having working channels that are flexible and axially expandable at their distal end so as to expand and contract as the channels bend about a remote neutral bending plane, thereby allowing the channels to bend without kinking and to exert a minimum degree of bending resistance on the endoscope. There is also a need for endoscope working channels with a durable lubricious inner lumen that allows for easy passage of an endoscopic accessory therethrough, an external surface that facilitates inserting and removing the endoscope. There is yet a further need for working channels that are inexpensive to manufacture so they can be used with a disposable endoscopic sheath and be disposed of after a single use.

SUMMARY OF THE INVENTION

It is an object of the present invention to provide a protective endoscopic sheath assembly having flexible, axially expandable, kink resistant working channels that substantially maintain their cross-sectional shape during acute endoscope articulation.

It is a further object of the present invention to provide an endoscopic sheath assembly with working channels that are positioned radially outward of an endoscope's neutral bending plane, wherein the working channels exert minimum resistance to bending of the endoscope.

It is yet a further object of the present invention to provide disposable endoscopic working channels constructed of inexpensive materials that maintain durability, flexibility, expandability, and lubricity characteristics so as to be economically feasible to dispose of the channels after a single endoscopic procedure.

These and other objects are provided by an endoscopic sheath assembly having working channels of the present invention. A preferred embodiment of the sheath assembly has a thin-walled flexible endoscope tube that is adapted to fit over, tightly surround and isolate at least a portion of an elongated, flexible endoscope used during therapeutic or diagnostic endoscopic procedures. The endoscope articulates about a neutral bending plane. The sheath assembly further has at least one kink resistant working channel, such as a biopsy channel, that is substantially parallel to the endoscope tube and is positioned radially outward of the neutral bending plane of the insertion tube when the endoscope is installed in the endoscope sheath assembly.

The biopsy channel has open proximal and distal ends that are adapted to allow an endoscopic accessory to pass therethrough. The biopsy channel further has a proximal section and an axially flexible distal section, wherein the proximal section extends distally from the proximal end of the channel and terminates at a transition area between the proximal and distal ends. The axially flexible distal section extends from the transition area to the open distal end. The distal section has an axially wound wire member forming an inner lumen of the channel's distal portion, and an elastomeric sleeve that fits over and tightly surrounds the wire member, thereby forming the exterior surface of the channel's distal portion.

The axially flexible distal section of the biopsy channel is preferably constructed with a flat wire spring member axially wound with a close pitch. The elastomeric sleeve is then interference fit over the flat wire spring to exert a radial compression force thereon. The proximal section of the biopsy channel is preferably constructed of composite tubes with a lubricious inner tube forming an inner lumen of the proximal section and an outer, kink-resistant, tube coaxially aligned with and secured around the inner tube.

The preferred sheath assembly also has kink-resistant air and water channels disposed in the sheath assembly substantially parallel to the biopsy channel and positioned radially outward of the neutral bending axis of the endoscope insertion tube. Each of the air and water channels have a composite construction with proximal section, which is made of a first material, that is connected to an axially flexible distal section at a transition area, wherein the distal section is made of a second material different from the first material.

DETAILED DESCRIPTION OF THE INVENTION

Figure 1:
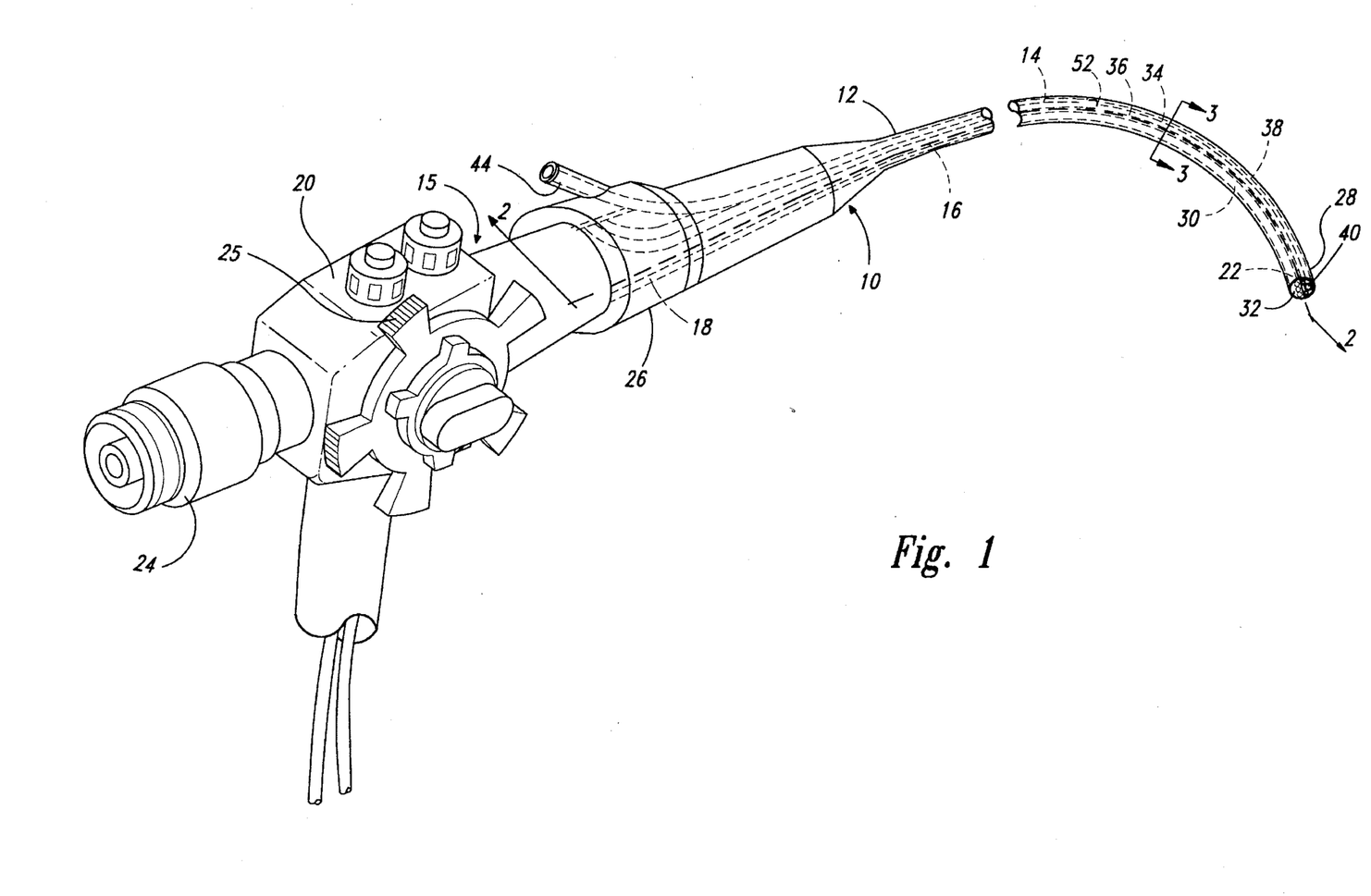
FIG. 1 is an isometric view of an endoscopic sheath assembly with working channels in accordance with the present invention installed over an insertion tube of an endoscope.

A preferred embodiment of the invention is described herein and shown in the attached drawings. As best seen in FIG. 1, a protective sheath assembly 10 having a thin-walled flexible endoscope tube 12 and working channels 14 is adapted for use with an endoscope 15 during therapeutic or diagnostic endoscopic procedures. The endoscope 15 has an elongated flexible insertion tube 16 that connects at its proximal end 18 to a control body 20. The insertion tube 16 has a conventional imaging device disposed therein for conveying an image from the insertion tube's distal end 22 to an eyepiece 24 connected to the control body 20. The control wires are located in the insertion tube 16 and connected to the distal end 22 and to control wheels 25 mounted on the control body 20. The control wires allow a user to move the distal end 22 left, right, up, down or any combination thereof, such that the insertion tube 16 will bend about its neutral bending plane. Thus, the distal portion of the insertion tube 16 can be articulated through short radius corners corresponding to contours of a body cavity.

The sheath assembly 10 has a proximal end 26 that surrounds the proximal end 18 of an insertion tube 16 installed in the endoscope tube 12, and a distal end 28 that surrounds with the distal end 22 of the insertion tube. The endoscope tube 12 is made of a thin, resilient elastomeric material that fits over and tightly surrounds the insertion tube 16 to isolate at least a part of the endoscope from an external environment. The thin, resilient elastomeric material creates a negligible resistance to bending of the insertion tube.

Figure 2:
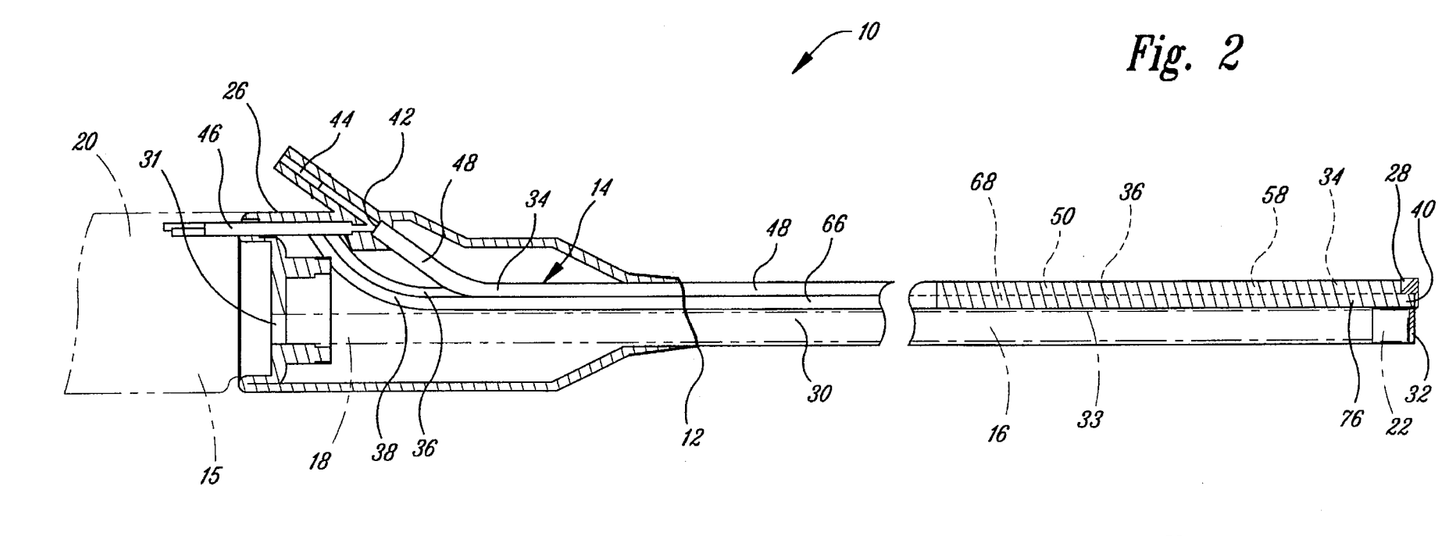
FIG. 2 is an enlarged, cross-sectional fragmented view taken substantially along line 2—2 of FIG. 1 with the endoscope shown in phantom.
Figure 3:
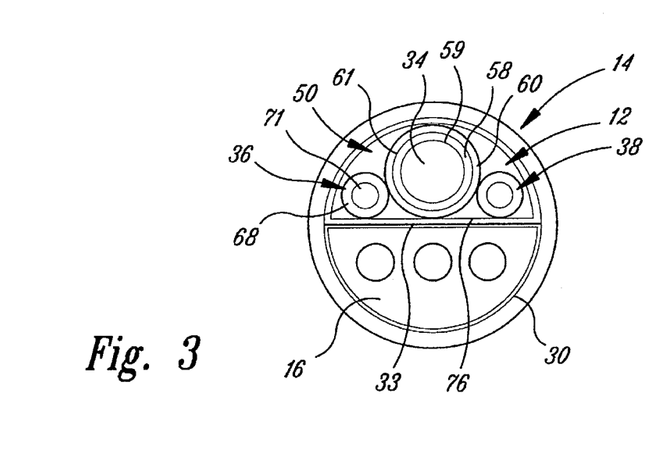
FIG. 3 is an enlarged cross-sectional view taken substantially along line 3—3 of FIG. 1.

As best seen in FIGS. 2 and 3, the endoscope tube 12 forms an endoscope channel 30 having an opening 31 at the proximal end 26 of the sheath assembly 10. The opening 31 is shaped and sized to receive the distal end 22 of the insertion tube 16 during installation. The distal end of the endoscope channel 30 is closed and sealed to prevent bodily fluids or other contaminants from entering the interior of the endoscope channel and contaminating the insertion tube 16.

The preferred endoscope tube 12 has a substantially circular cross-section and is shaped and sized to receive a non-cylindrical or "D" shaped insertion tube, as disclosed in U.S. Pat. No. RI 34,110. As such, the insertion tube 16 fills approximately half of the cross-section of the endoscope tube 12, with curved portion of the insertion tube 16 engaging the axial walls of the endoscope tube 12. The remaining half of the cross-section is substantially filled by the working channels 14.

Referring to FIGS. 2–7, the working channels 14 of the sheath assembly 12 include a biopsy channel 34, a water channel 36 and an air channel 38. The biopsy channel 34 is a kink-resistant tube positioned between the axial sidewall of the endoscope tube 12 and the flat surface of the insertion tube 16. The biopsy channel 34 extends along the length of the endoscope tube 12 substantially parallel to the endoscope channel 30. As best seen in FIG. 2, the biopsy channel 34 has an open distal end 40 that sealably engages an opening in the sheath assembly's distal end 28, wherein the opening is shaped and sized to allow an endoscopic accessory to pass therethrough. An open proximal end 42 of the biopsy channel 34 attaches to and is coaxially aligned with a biopsy port 44 at the proximal portion of the sheath assembly 12. The biopsy port 44 is a tubular member adapted to receive and guide the distal end of an endoscopic accessory into the open proximal end 42 of the biopsy channel 34 as the endoscopic accessory is inserted into the biopsy channel before or during an endoscopic procedure. The endoscopic accessory can be any one of a wide variety of accessories having tools thereon to perform different endoscopic tasks in addition to taking tissue samples or other biopsies.

The biopsy channel 34 is also coupled at its proximal end 42 to a suction line 46 that is attached at one end to the base of the biopsy port 44 and is connected at its other to a remote suction source. The suction source is used to create suction within the biopsy channel 34 so material may be sucked through the open distal end 40 along the length of the biopsy channel and out the suction line 46. Accordingly, the biopsy channel 34 of the preferred embodiment acts as a biopsy/suction channel. However, the biopsy channel of the subject invention can also be used solely as a biopsy channel with suction being provided by a different manner.

Figure 4:
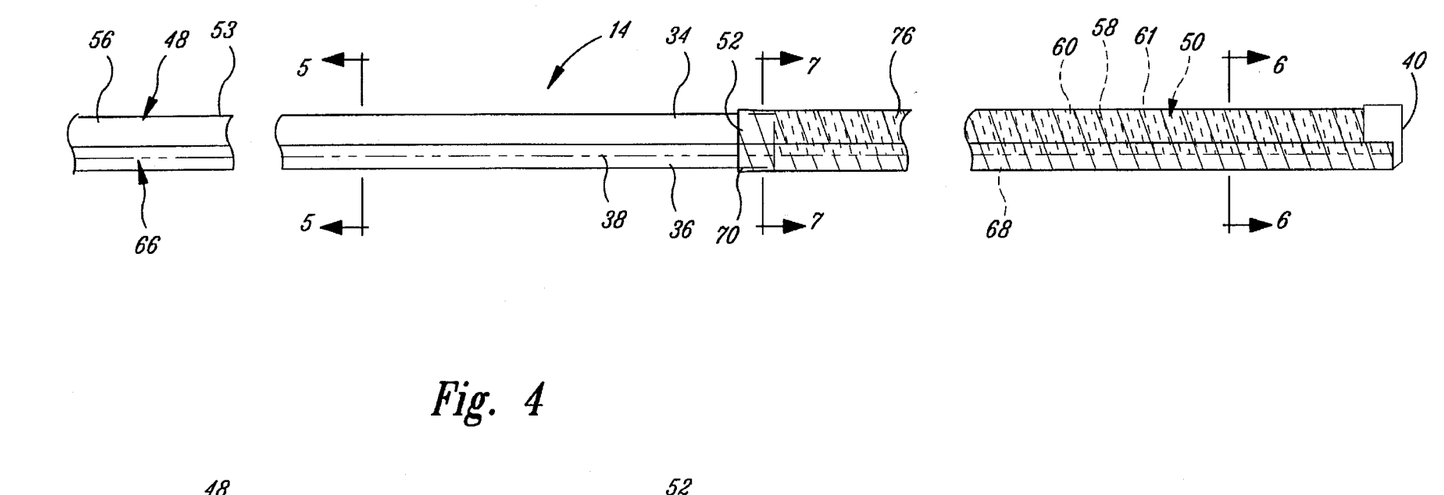
FIG. 4 is an enlarged, fragmented side elevation view of the working channels of FIG. 1, including a biopsy channel, an air channel, and a water channel removed from the sheath.
Figure 5:
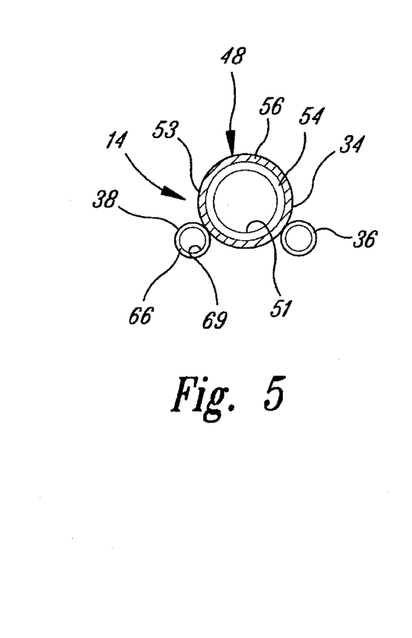
FIG. 5 is an enlarged cross-sectional view taken substantially along line 5—5 of FIG. 4.
Figure 8:
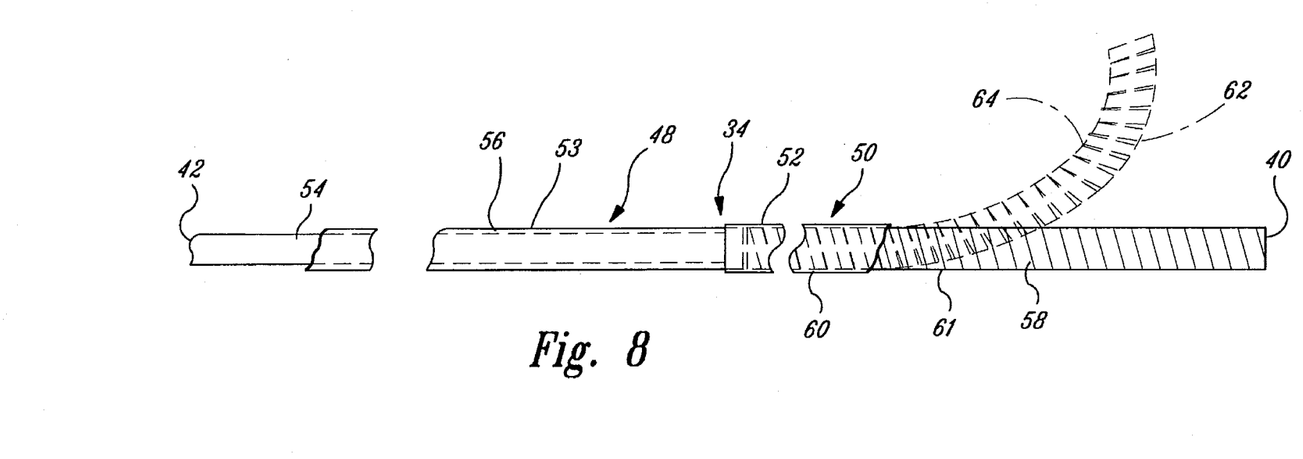
FIG. 8 is a fragmented side elevation view of the biopsy/suction channel of FIG. 4 removed from the other channels.

As best seen in FIGS. 4, 5, and 8, the biopsy channel 34 has a proximal section 48 that forms approximately two thirds of the length of the biopsy channel, and an expansion section 50 that forms the remaining third of the biopsy channel's length. The proximal section 48 has two concentrically aligned tubes, including an inside tube 54 with an inside surface 51 forming an inner lumen of the proximal section, and a coaxially aligned outside tube 56 surrounding the inside tube 54.

The inside tube 54 is preferably a flexible, extruded polyethylene tube with the inner lumen sized and shaped to allow an endoscopic accessory to pass therethrough. The inner lumen also is sized so that bodily fluids and other material can be sucked through the proximal section. The inside tube 54 provides a durable and lubricious inside surface 51 that allows for smooth passage of the endoscopic accessory with minimum frictional resistance.

The outside tube 56 of the proximal section 48 is a flexible, kink-resistant, extruded tube preferably made of polyvinylchloride ("PVC") that is secured with conventional adhesive to the outer surface of the inside tube 54. The outside tube 56 provides a sufficiently lubricious outer surface 53 of the proximal section 48 that allows the biopsy channel 34 to move and slip relative to the air and water channels, 36 and 38, and the endoscope tube 12 during endoscope articulation. The outside tube 56 is an inexpensive tube that bonds easily to the inside tube 54, thereby simplifying manufacturing of the proximal section 48. In addition, the outside tube 56 and the inside tube 54 are air impervious, so suction can be maintained in the proximal section of the biopsy channel 34. Although the preferred embodiment uses polyethylene tubing and PVC tubing, the inside tube could be made from a different durable, lubricious material, other than polyethylene, and the outside tube could be made from durable material that provides a substantially kink-resistant assembly, which maintains its cross-sectional shape during endoscopic articulation.

Figure 6:
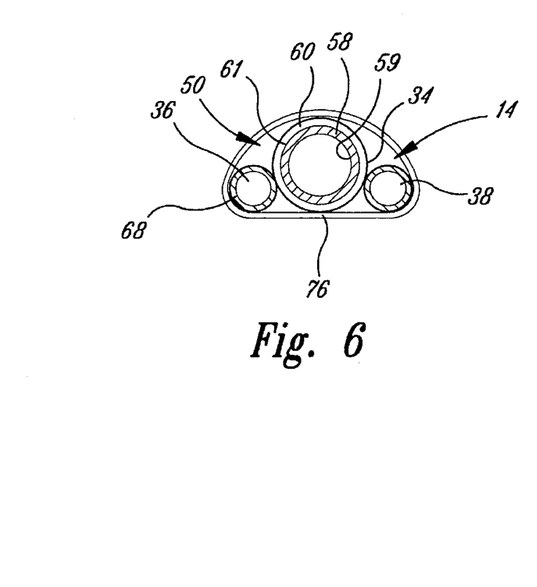
FIG. 6 is an enlarged cross-sectional view taken substantially along line 6—6 of FIG. 4.

As best seen in FIGS. 4, 6, and 8, the expansion section 50 of the biopsy channel 34 connects to the distal end of the proximal section 48 and extends to the open distal end 40 of the biopsy channel. The expansion section 50 has a two-part, concentric tubular construction. An axially wound spring 58, or other filament, has an inner surface 59 that forms an inner lumen of the expansion section 50. The inner lumen of the spring 58 extends the length of the expansion section 50 and is shaped and sized to allow the endoscopic accessory to pass therethrough during an endoscopic procedure. An outside elastomeric sleeve 60 fits over and tightly surrounds the spring 58 along its length and exerts a radial compression force on the spring to maintain a substantially round cross-section of the expansion section. In the preferred embodiment, the spring 58 is a closely wound, stainless steel, flat wire spring wherein adjacent windings of the spring abut each other but do not overlap when the expansion section 50 is straight and not in a bent configuration.

The inner lumen formed by the close-wound, flat wire spring 58 has a smooth, lubricious, inner surface 59 that prevents the endoscopic accessory or tool from hanging up when the endoscopic accessory is passed through the expansion section 50 bent around a tight corner. The spring 58 provides a very durable inner lumen along the entire expansion section 50, which alleviates the risk of being damaged by the endoscopic accessory. The spring 58 also provides kink-resistance and minimizes the diameter change of the inner lumen as the spring bends and stretches during acute endoscope articulation, because of an increased support of the expansion section's axial walls. The preferred embodiment uses a stainless steel, axially would flat wire spring, although other axially wound springs, such as round or oval wire springs, can be used instead.

The elastomeric sleeve 60 on the expansion section 50 is preferably a latex rubber sleeve that is interference fit over the outside surface 61 of the spring 58. The latex robber is axially expandable to accommodate stretching and contracting of the expansion section 50, described in detail below. The latex rubber sleeve is also air impervious so suction can be maintained within expansion section 50 of the biopsy channel 34. Other expandable material, such as CFlex™, Krayton™, or another elastomer having a 500% or better elongation may be used in place of the latex robber sleeve 60 in order to stretch and contract with bending of the biopsy channel 34.

The kink-resistant expansion section 50 is constructed to be axially expandable and contractible so the biopsy channel 34 can be easily bent when the endoscope insertion tube 16 is bent around the tight comers while creating a minimal resistance to such bending. For example, the biopsy channel 34 must expand and contract significantly when the sheath assembly 10 is installed over the insertion tube 16, as seen in FIG. 1, and the distal portion of the insertion tube is articulated about its neutral bending plane, and the expansion section 50 of the biopsy channel 34 must expand or contract, because it is also bent about the same neutral bending plane, as shown in FIG. 1. If the biopsy channel 34 is positioned on the side of the insertion tube 16 forming the outside of the curve, the expansion section axially expands and adjacent windings of the spring 58 slightly separate and the elastomeric sleeve 60 expands and stretches over the spring, as seen in phantom in FIG. 7. The adjacent windings of the spring 58 on the outside 62 of the curve formed by the bent biopsy channel 34 and insertion tube 16 experience the greatest degree of axial expansion, and experience the greatest degree of separation. The adjacent windings of the spring 58 inside of the curve 64 are also separated, but to a lesser degree. Conversely, when the biopsy channel 34 is positioned on the side of the insertion tube 16 forming the inside of the curve, the adjacent windings of the spring 58 and the elastomeric sleeve 60 are compressed and the elastomeric sleeve 60 contracts rather than buckling or getting pinched between the windings.

Figure 7:
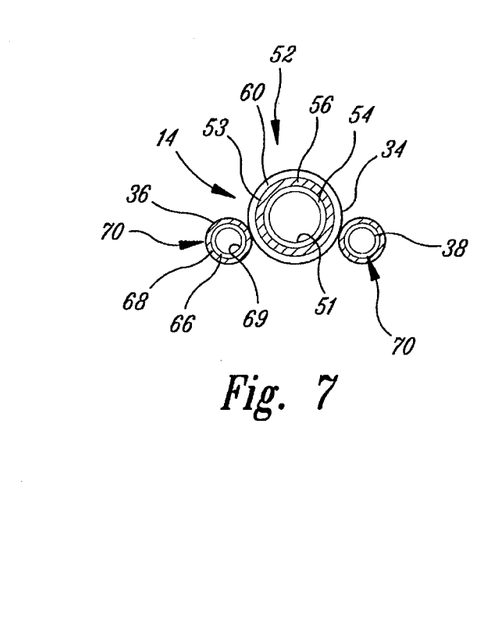
FIG. 7 is an enlarged cross-sectional view taken substantially along line 7—7 of FIG. 4.

As best seen in FIGS. 4, 7, and 8, the expansion section 50 is securely attached to the distal end of the proximal section 48 at a transition area 52. The elastomeric sleeve 60 of the expansion section 50 is interference fit over a portion of the outside tube 56 so as to form a lap joint. The elastomeric sleeve 60 is also bonded or otherwise securely attached to the proximal section 48 to prevent inadvertent separation. The axially wound spring 58 abuts the proximal section 48 so the inner lumen of the proximal section is coaxially aligned with the inner lumen of the expansion section 50. These two inner lumen have approximately the same diameter to provide a smooth transition between the proximal and expansion sections 48 and 50 at the transition area 52.

Figure 9:
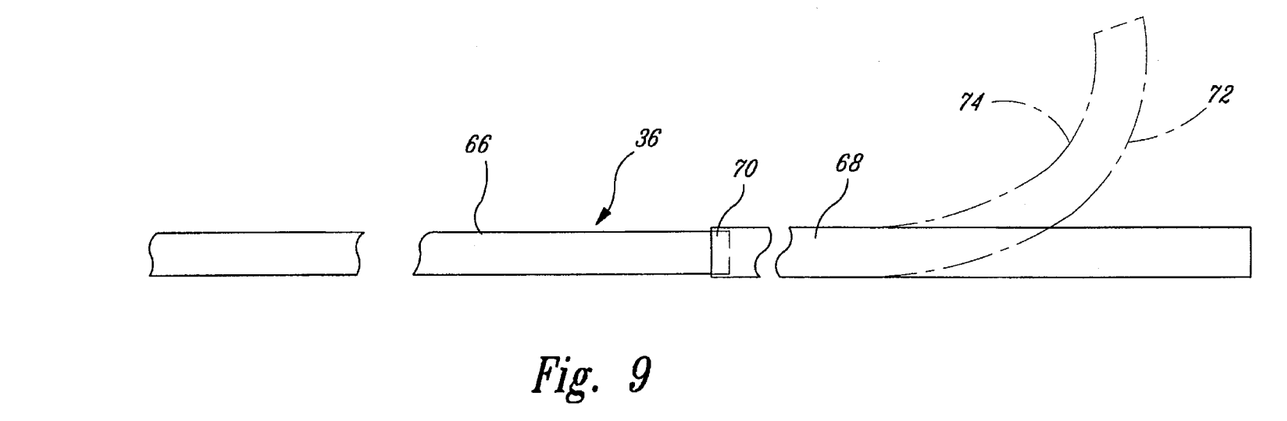
FIG. 9 is a fragmented side elevation view of the water channel of FIG. 4 removed from the other channels.

As best seen in FIGS. 4 and 9, the water channel 36 has a proximal section 66 and an expansion section 68 that are connected to each other at a transition area 70. The water channel 36 and air channel 38 of the preferred embodiment have the same construction, so only the water channel 36 will be described in detail below for purposes of brevity, although it is to be understood that the description of the water channel is equally applicable to the air channel, with the exception of the material flowing therethrough.

The proximal section 66 of the water channel 36 extends approximately two thirds of the water channel's length and is constructed of a kink-resistant PVC robe, or the like. The PVC tube has an inner surface 69 that forms an inner lumen that allows a flow of material to freely pass through the proximal section 66 during an endoscopic procedure. The proximal section 66 has a thickness that is sufficient to prevent kinking as the water channel 36 is bent about the neutral bending plane of the insertion tube 16. However, the thickness of the PVC tube is such that the cross-section of the water channel 36 can change shape without kinking upon acute endoscope articulation. This change of cross-sectional shape reduces resistance to the bending of the insertion tube. The diameter of the proximal section's inner lumen is determined by the required flow of material for an endoscopic procedure. In the preferred embodiment, the proximal section 66 of the water channel 36 has a smaller diameter than the diameter of the biopsy channel's proximal section 48.

The expansion section 68 of the water channel 36 is preferably a thick-walled, elastomeric tubular extrusion that is connected to the proximal section 66 at the transition area 70 by a conventional lap joint, wherein the expansion section overlaps the proximal section. The expansion section 68 extends along the remaining third of the water channel 36. The elastomeric tube has an inner surface 71 that forms an inner lumen, which allows the flow of material to freely pass through the expansion section 68 during the endoscopic procedure. The distal end of the expansion section 68 is open and sealably engages the distal end 28 of the endoscope tube 12, as shown in FIG. 2, so the water can flow out of the sheath assembly 10 into a patient's body cavity.

The elastomeric expansion section 68 is adapted to flex and expand axially and radially while maintaining a degree of kink resistance, and while allowing the cross-section of the expansion section to change shapes that will permit the water to freely flow therethrough. For example, when the expansion section 68 of the water channel 36 is bent during endoscope articulation, as shown in phantom in FIG. 8, and the water channel is on the outer side of the curved insertion tube, the outside 72 and the inside 74 of the bent section are expanded axially. When the water channel 36 is on the inner side of the curved insertion tube, the outside 72 and the inside 74 of the bent section are compressed without buckling or folding. Accordingly, the elastomeric extrusion of the expansion section 68 stretches and contracts as the water channel 36 is bent about the insertion tube's neutral bending plane. In addition, the water channel 36 exerts minimal resistance to bending motion by the insertion tube. Although the preferred embodiment described herein provides air and water channels, it is to be understood that the sheath assembly of the present invention can be used with or without the air or water channels as necessary for different endoscopic procedures.

As indicated above, the biopsy channel 34 and the air and water channels 36 and 38 are disposed within the endoscope tube 12, as best seen in FIGS. 2 and 3, so they are aligned adjacent to each other in a substantially D-shaped formation. This D-shaped formation combines with the non-cyclical insertion tube 16 to form an endoscopic assembly with a substantially round cross-sectional area. The expansion section 50 of the biopsy channel 34 and the expansion sections 68 of the air and water channels 36 are bundled together in the D-shaped formation by a wrap 76. The wrap 76 holds the channels 34, 35, and 38 together and isolates their expansion sections 50 and 60 from the insertion tube 16 installed in the endoscope tube 12. The wrap 76 also maintains alignment of the channels 34, 36, and 38 so that they do not twist or become entangled during use of the sheath assembly 10. The wrap 76 is preferably a low friction, urethane strip that is spirally wrapped around the expansion sections 50 and 68 of the channels 34, 36, and 38, as best seen in FIGS. 4 and 6, such that adjacent windings of the wrap abut each other without overlapping. The urethane spiral wrap 76 provides a lower coefficient of friction between the insertion tube 16 and the channels 34, 36, and 38 during installation or removal of the insertion tube.

When the insertion tube bends about its neutral bending plane and the expansion sections 50 and 68 of the channels 34, 36, and 38 are bent about the same neutral bending plane (not shown), the adjacent windings of the spiral wrap 76 slightly separate when the channels are on the outer side of the curved insertion tube, and the adjacent windings are compressed against each other when the channels are on the inner side of the curved insertion tube. As such, the spiral wrap 76 provides a minimal resistance to the bending of the sheathed insertion tube. In addition, the expansion sections 50 and 68 of the channels 34, 36, and 38 can move axially through a limited degree to even further facilitate the bending action of the sheath assembly 10 while exerting a minimal resistance to bending of the insertion tube 16.

A dry lubricant material can also be added on the exterior surfaces of the expansion sections 50 and 68 under the wrap 76 to enable the channels to slip against each other when the sheath assembly 10 is bent. In the alternative, an anti-friction coating, such as silicone oil or the like, can be used in place of the dry lubricant.

In an alternate embodiment of the invention, the elastomeric sleeve on the expansion section 50 of the biopsy channel 34 and the elastomeric extrusions of the expansion sections 68 of the air and water channels 36 and 38 have lubricious plasticizers or other anti-friction additives incorporated into the elastomeric material of the sections. These plasticizers or anti-friction additives assist in reducing friction between the channels when they are positioned in the endoscope tube 12 adjacent to the insertion tube, with or without the spiral wrap around to the channels.

The endoscope tube 12 and working channels 14 of the preferred embodiment described above are disposable, because they are constructed with inexpensive, readily available materials, including PVC tubes, elastomeric tubes, and an axially wound spring, and they can be assembled in fast and inexpensive manner. Thus, the cost of each sheath assembly can be kept relatively low. The endoscope can be slipped out of a used sheath and working channel assembly and into a new sheath assembly and be ready for the next endoscopic procedure in a matter of minutes, and the used sheath and working channel assembly disposed of in a proper medical waste receptacle.

Numerous modifications and variations of the working channels for a disposable sheath for an endoscope disclosed herein will occur to those skilled in the art in view of this disclosure. For example, the proximal portion of the working channels may be removably connected to the expansion sections of the working channels such that the proximal sections may be removable and adaptable for use with expansion sections that have specific limited functions to perform different aspects of an endoscopic procedure. Therefore, it is to be understood that these modifications and variations, and equivalents thereof may be practiced while remaining within the spirit and scope of the invention as defined in the following claims.

We claim:

1. An endoscopic sheath assembly having axial side walls and proximal and distal ends, the sheath assembly being adapted for use with an elongated, flexible endoscope having a neutral bending plane, the assembly comprising:

a thin walled flexible endoscope tube adapted to fit over and tightly surround the endoscope to isolate at least a portion of the endoscope from an external environment, said endoscope tube having an opening at said proximal end for receiving the distal end of the endoscope and closed distal end; and a kink-resistant biopsy channel substantially parallel to said endoscope tube and positioned radially outward from the neutral bending plane, said biopsy channel having open proximal and distal ends and being adapted to allow endoscopic accessories to pass therethrough, said biopsy channel comprising a proximal section, an axially flexible distal section, and a transition area extending between and interconnecting said proximal section and said axially flexible distal section, said axially flexible distal section comprising an axially wound wire member forming a lumen adapted to allow an endoscopic instrument to pass therethrough, and an elastomeric sleeve that fits over and tightly surrounds said wire member; said axially flexible distal section being substantially more flexible than said proximal section.

2. The endoscopic sheath of claim 1 wherein said axially wound wire member is a close-wound spring.

3. The endoscopic sheath of claim 2 wherein said close-wound spring is a flat wire spring.

4. The endoscopic sheath of claim 1 wherein said elastomeric sleeve exerts a radial compression force on said wire member.

5. The endoscopic sheath of claim 1 wherein said proximal section comprises first and second coextruded tube members, said first tube member being a lubricious material forming an inner diameter of said proximal section and said second tube member being a kink-resistant outer tube secured around said first tube member.

6. The endoscopic sheath of claim 5 wherein said first tube member is a polyethylene tube.

7. The endoscopic sheath of claim 5 wherein said second tube member is a polyvinyl chloride tube bonded to said first tube member.

8. The endoscopic sheath of claim 1 wherein said biopsy channel has axial walls that are air impervious and adapted to form an endoscopic suction channel.

9. An endoscopic sheath assembly having axial side walls and proximal and distal ends, the sheath assembly being adapted for use with an elongated, flexible endoscope having a neutral bending plane, during a therapeutic or diagnostic endoscopic procedure, the assembly comprising:

a thin walled flexible endoscope tube adapted to fit over and tightly surround the endoscope to isolate at least a portion of the endoscope from an external environment, said endoscope tube having an opening at said proximal end for receiving the distal end of the endoscope and closed distal end;

a kink-resistant biopsy channel substantially parallel to said endoscope tube and positioned radially outward from the neutral bending plane, said biopsy channel having open proximal and distal ends and being adapted to allow endoscopic accessories to pass therethrough, said biopsy channel comprising a proximal section and an axially flexible distal section, said proximal section extending along the proximal portion of the sheath and terminating at a transition area, and said axially flexible distal section extending from said transition area to said open distal end, said axially flexible distal section comprising an axially wound wire member forming a lumen adapted to allow an endoscopic instrument to pass therethrough, and an elastomeric sleeve that fits over and tightly surrounds said wire member; and an air channel and a water channel extending along the length of the sheath substantially parallel to said biopsy channel, each of said air and water channel having a proximal section formed by a first material and an axially flexible distal section connected to said proximal section, said distal section being formed by a second material different from said first material.

10. The endoscopic sheath of claim 9 wherein said first material is a polyvinyl chloride extrusion and said second material is a thick-walled, flexible elastomeric extrusion.

11. The endoscopic sheath of claim 9 wherein said expansion section of said biopsy channel and said distal sections of said air and water channels have approximately the same length.

12. The endoscopic sheath of claim 9, further comprising a wrapping member around said biopsy channel and said air and water channels to hold said channels together as a bundle and to at least partially isolate said channels from the endoscope.

13. The endoscopic sheath of claim 12 wherein said wrapping member is spirally wrapped around said expansion section of said biopsy channel and said distal sections of said air and water channels.

14. The endoscopic sheath of claim 13 wherein said wrapping member is a urethane material.

15. The endoscopic sheath of claim 9, further comprising a coating on said distal sections of said air and water channels to reduce friction therebetween.

16. The endoscopic sheath of claim 15 wherein said coating is silicon.

17. The endoscopic sheath of claim 15 wherein said coating is Teflon.

18. Endoscopic sheath channels disposed within an endoscopic sheath having axial side walls and proximal and distal ends, the sheath being adapted for use with an elongated, flexible endoscope, the channels comprising:

a kink-resistant suction and biopsy channel having open proximal and distal ends, a proximal section, an axially flexible distal section, and a transition area extending between and interconnecting said proximal section and said axially flexible distal section, said distal section comprising an axially wound wire member and an elastomeric sleeve that fits over and tightly surrounds said wire member, said axially wound wire member forming an tubular area that allows material and endoscopic accessories to pass therethrough, said axially flexible distal section being substantially more flexible than said proximal section;

an air channel adjacent to said suction and biopsy channel, said air channel having open proximal and distal ends, a proximal section, a distal section, and a second transition area extending between and interconnecting said proximal section and said distal section of said air channel, said distal section of said air channel being a flexible, thick-walled elastomeric extrusion; and a water channel adjacent to said suction and biopsy channel, said water channel having open proximal and distal ends, a proximal section, a distal section, and a third transition area extending between and interconnecting said proximal section and said distal section of said water channel, said distal section of said water channel being a flexible, thick-walled elastomeric extrusion.

19. The endoscopic sheath channels of claim 18 wherein said axially wound wire member is a close-wound spring.

20. The endoscopic sheath channels of claim 19 wherein said close-wound spring is a flat wire spring.

21. The endoscopic sheath channels of claim 18 wherein said proximal section of said suction and biopsy channel comprises first and second coextruded tube members, said first tube member being a lubricious material forming an inner diameter of said proximal section and said second tube member being a kink-resistant outer tube secured around said first tube member.

22. The endoscopic sheath channels of claim 21 wherein said second tube member is bonded to said first tube member.

23. The endoscopic sheath channels of claim 21 wherein said first tube member is a polyethylene tube.

24. The endoscopic sheath channels of claim 21 wherein said second tube member is a polyvinyl chloride tube.

25. The endoscopic sheath channels of claim 18 wherein said distal sections of said suction and biopsy channel and said air and water channels have approximately the same length.

26. The endoscopic sheath channels of claim 18, further comprising a wrapping member around said suction and biopsy channel and said air and water channels to hold said channels together as a bundle and to at least partially isolate said channels from the endoscope.

27. The endoscopic sheath of claim 26 wherein said wrapping member is spirally wrapped along said distal sections of said biopsy and suction channel and said air and water channels.

28. The endoscopic sheath of claim 26 wherein said wrapping member is a urethane material.

29. The endoscopic sheath of claim 18, further comprising an outer coating on said distal sections of said biopsy and suction channel and said air and water channels to reduce friction therebetween.

30. The endoscopic sheath of claim 29 wherein said coating is silicon.

31. The endoscopic sheath of claim 29 wherein said coating is Teflon.

* * * * *